United States Patent
Becker et al.

(10) Patent No.: US 11,090,486 B2
(45) Date of Patent: *Aug. 17, 2021

(54) ROOT CANAL TREATMENT

(71) Applicant: MedicN.R.G. Ltd., Kibbutz Afikim (IL)

(72) Inventors: Arik Becker, Kibbutz Afikim (IL); Haim Rozenboim, Natania (IL); Haim Levy, Pardes Hana (IL); Simon Rothenstein, Rosh HaAyin (IL); Gregory Berdichevsky, Petach-Tikva (IL); Omer Zeharhary, Kibbutz Afikim (IL)

(73) Assignee: MDT MICRO DIAMOND TECHNOLOGIES LTD, Afula (IL)

(*) Notice: Subject to any disclaimer, the term of this patent is extended or adjusted under 35 U.S.C. 154(b) by 483 days.

This patent is subject to a terminal disclaimer.

(21) Appl. No.: 15/492,087

(22) Filed: Apr. 20, 2017

(65) Prior Publication Data

US 2017/0216579 A1    Aug. 3, 2017

Related U.S. Application Data

(63) Continuation of application No. 12/773,061, filed on May 4, 2010, now Pat. No. 9,629,691, which is a
(Continued)

(51) Int. Cl.
    *A61N 1/05*      (2006.01)
    *A61C 19/04*      (2006.01)
    (Continued)

(52) U.S. Cl.
    CPC .............. *A61N 1/0548* (2013.01); *A61C 5/40* (2017.02); *A61C 5/44* (2017.02); *A61C 5/50* (2017.02);
(Continued)

(58) Field of Classification Search
CPC .... A61C 5/44; A61C 5/40; A61C 5/50; A61C 19/041; A61C 19/042; A61N 1/058; A61N 1/325; A61B 18/14
See application file for complete search history.

(56) References Cited

U.S. PATENT DOCUMENTS 1,713,971 A * 5/1929 Lowry .................. A61C 5/40
                                                  606/49
2,121,875 A * 6/1938 Kruse ................... A61L 2/238
                                                  205/74
(Continued)

FOREIGN PATENT DOCUMENTS

CN          1224339        7/1999
NL            39132          5/1936
(Continued)

OTHER PUBLICATIONS

Communication Pursuant to Article 94(3) EPC dated Mar. 10, 2016 From the European Patent Office Re. Application No. 09764904.0.
(Continued)

*Primary Examiner* — Heidi M Eide

(57) ABSTRACT

A device for disinfecting and/or sterilization of a dental cavity includes: an electrode pair that extends into the cavity to provide current along a portion of the cavity; and a controller that sends controlled electrical energy to the cavity via current flowing between the electrodes when located in the cavity, thereby to provide electrical energy for disinfection and/or sterilization.

20 Claims, 10 Drawing Sheets

Related U.S. Application Data continuation-in-part of application No. PCT/IL2009/001048, filed on Nov. 5, 2009.

(60) Provisional application No. 61/193,204, filed on Nov. 5, 2008.

(51) Int. Cl.
*A61C 5/40* (2017.01)
*A61C 5/44* (2017.01)
*A61C 5/50* (2017.01)
*A61N 1/32* (2006.01)
*A61B 18/14* (2006.01)

(52) U.S. Cl.
CPC .......... *A61C 19/041* (2013.01); *A61C 19/042* (2013.01); *A61N 1/325* (2013.01); *A61B 18/14* (2013.01)

(56) References Cited

U.S. PATENT DOCUMENTS

| | | | |
|---|---|---|---|
| 2,276,623 A | 3/1942 | Meiman | |
| 2,931,947 A * | 4/1960 | Frankfruengel | A01J 7/02 315/111.01 |
| 3,916,529 A | 11/1975 | Mousseau | |
| 4,447,206 A | 5/1984 | Ushiyama | |
| 4,597,388 A * | 7/1986 | Koziol | G10K 15/06 606/107 |
| 4,886,075 A * | 12/1989 | Jones | A61N 1/20 607/134 |
| 5,421,727 A * | 6/1995 | Stevens | A61C 5/40 433/102 |
| 5,964,754 A | 10/1999 | Osypka | |
| 6,179,824 B1 | 1/2001 | Eggers et al. | |
| 6,319,007 B1 * | 11/2001 | Livaditis | A61B 18/1402 433/224 |
| 6,482,008 B2 | 11/2002 | Perdomini et al. | |
| 6,497,704 B2 | 12/2002 | Ein-Gal | |
| 6,971,878 B2 | 12/2005 | Pond | |
| 7,270,661 B2 * | 9/2007 | Dahla | A61B 18/148 606/41 |
| 7,794,458 B2 * | 9/2010 | McIntyre | A61B 18/1477 606/41 |
| 2002/0058232 A1 | 5/2002 | Weiss et al. | |
| 2002/0058936 A1 | 5/2002 | Avrahami et al. | |
| 2002/0192627 A1 * | 12/2002 | Lee | G09B 23/283 434/263 |
| 2004/0101809 A1 * | 5/2004 | Weiss | A61C 5/40 433/224 |
| 2004/0219482 A1 | 11/2004 | Bina et al. | |
| 2007/0207445 A1 | 9/2007 | Pitel | |
| 2008/0097425 A1 | 4/2008 | Truckai | |
| 2008/0187880 A1 | 8/2008 | Becker et al. | |
| 2009/0043293 A1 * | 2/2009 | Pankratov | A61B 18/203 606/9 |

FOREIGN PATENT DOCUMENTS

| | | |
|---|---|---|
| WO | WO 97/46170 | 12/1997 |
| WO | WO 2008/114243 | 9/2008 |
| WO | WO 2008/114244 | 9/2008 |
| WO | WO 2010/052717 | 5/2010 |

OTHER PUBLICATIONS

Communication Pursuant to Article 94(3) EPC dated Feb. 23, 2017 From the European Patent Office Re. Application No. 09764904.0. (4 Pages).
Communication Pursuant to Article 94(3) EPC dated May 28, 2015 From the European Patent Office Re. Application No. 09764904.0.
International Preliminary Report on Patentability dated May 19, 2011 From the International Bureau of WIPO Re. Application No. PCT/2009/001048.
International Search Report and the Written Opinion dated Mar. 11, 2010 From the International Searching Authority Re. Application No. PCT/IL2009/001048.
Office Action dated Sep. 16, 2013 From the State Intellectual Property Office of the People's Republic of China Re. Application No. 200980153699.2 and Its Translation Into English.
Official Action dated Dec. 5, 2014 From the US Patent and Trademark Office Re. U.S. Appl. No. 12/773,061.
Official Action dated Jun. 9, 2015 From the US Patent and Trademark Office Re. U.S. Appl. No. 12/773,061.
Official Action dated Oct. 11, 2012 From the US Patent and Trademark Office Re. U.S. Appl. No. 12/773,061.
Official Action dated Jun. 14, 2012 From the US Patent and Trademark Office Re. U.S. Appl. No. 12/773,061.
Official Action dated Aug. 16, 2011 From the US Patent and Trademark Office Re. U.S. Appl. No. 12/773,061.
Official Action dated Mar. 25, 2014 From the US Patent and Trademark Office Re. U.S. Appl. No. 12/773,061.
Official Action dated Jun. 29, 2016 From the US Patent and Trademark Office Re. U.S. Appl. No. 12/773,061.
Official Action dated Apr. 30, 2013 From the US Patent and Trademark Office Re. U.S. Appl. No. 12/773,061.
Translation of Office Action dated Apr. 16, 2013 From the State Intellectual Property Office of the People's Republic of China Re. Application No. 200980153699.2.
Translation of Search Report dated Apr. 16, 2013 From the State Intellectual Property Office of the People's Republic of China Re. Application No. 200980153699.2.
Dictionary.com "wound", The American Heritage® Idioms Dictionary, 12 P., 1995.

* cited by examiner

ROOT CANAL TREATMENT

RELATED APPLICATIONS

This application is a continuation of U.S. patent application Ser. No. 12/773,061, filed on May 4, 2010, which is continuation-in-part (CIP) of PCT Patent Application No. PCT/IL2009/001048 having International Filing Date of Nov. 5, 2009, which claims the benefit of priority of U.S. Provisional Patent Application No. 61/193,204 filed on Nov. 5, 2008. The contents of the above applications are all incorporated by reference as if fully set forth herein in their entirety.

FIELD AND BACKGROUND OF THE INVENTION

The present invention relates to a device and method for treatment of a dental cavity such as a root canal and, more particularly, but not exclusively to a device for sterilizing a root canal.

A root canal is the commonly used term for the main canals within the dentine of the tooth. These are part of the natural cavity within a tooth that consists of the dental pulp chamber, the main canals, and sometimes more intricate anatomical branches that may connect the root canals to each other or to the root surface of the tooth. Root canals are filled with a highly vascularized, loose connective tissue, the dental pulp. This sometimes becomes infected and inflamed, generally due to caries or tooth fractures that allow microorganisms, mostly bacteria from the oral flora or their byproducts, access to the pulp chamber or the root canals. The infected tissue is removed by a surgical intervention known as endodontic therapy, more commonly known as root canal treatment.

Removal and disinfection procedures are not always effective at removing individual bacteria, but it is even more difficult to remove bacterial films. Nevertheless complete removal of bacteria or sterilization of the canal prior to sealing the root canal is a necessary condition for a successful outcome to the treatment.

Known systems insert cleaning (disinfecting) fluids into the root canal but such fluids are highly toxic. Furthermore they have to be present in the root canal for a relatively large amount of time. In addition the fluid must reach every part of the root canal, something which cannot be guaranteed. In some cases, particularly where infection is already present, the treatment must be repeated several times before the root canal can be sealed. The method takes time and depends very much on the expertise of the dentist carrying out the treatment.

A further disadvantage of the above system is that bubbles or air pockets tend to occur, especially in the deeper parts of the root canal or where root canal passages are not straight, and the air pockets tend to prevent the cleaning fluid from making contact with all surfaces.

Other systems place an electrode inside the root canal and another electrode outside the tooth and pass a current between the two, closing the circuit via the human body. The electromagnetic field and in some case the temperature kills bacteria, but the effectiveness is limited because often the conditions in the canal are not ideal. This is particularly the case when the electrode is far from the apical aria. One version uses 500 Watts of power, at a frequency of 300-KHz, in order to create a current path from the apical aria of the root canal to the external electrode, through the patient's flesh. A disadvantage of this system is that much of the power provided goes to setting up the current path and not to carrying out the sterilization. Furthermore the sterilization effect is not uniform over the root canal, and requires exceptional skill on the part of the dentist in order to be successful. Furthermore the resistance provided by the human body varies between individuals, making it impossible to control the power level in given cases. Thus a higher than designed resistance may reduce the output and vice versa. Furthermore the power increases with proximity to the apical aria, due to the reduced distance between the two ends of the probe or electrode and in some cases a current overload may result, causing pain to the patient. Thus it is impossible to control the power and you may either expose the client to sharp, pain or you may fail to provide sufficient power to destroy all the bacteria.

In particular, efforts to ensure that the effect is evenly distributed over the root canal are complicated by the need to avoid the root canal apex. The apex contains healthy tissue which should not be damaged.

There is thus a widely recognized need for, and it would be highly advantageous to have, a method of root canal sterilization that is devoid of the above limitations.

SUMMARY OF THE INVENTION

According to some embodiments of a first aspect of the present invention there is provided a device for disinfecting and/or sterilization of a dental cavity comprising:
  an electrode pair adapted to extend into said cavity to provide current along at least a portion of the cavity; and
  a controller configured for sending controlled electrical energy to said cavity via current flowing between the electrodes when located in said cavity, thereby to provide electrical energy for said disinfection and/or sterilization.

In an embodiment of the invention a first electrode of said electrode pair forms a central axis and a second electrode of said electrode pair is coiled about said central axis.

Optionally, said first electrode is controllably extendable along said axial direction, thereby to vary a length of a gap between said first electrode and said second electrode.

Optionally, said controller is configured to adjust a level of energy released within said cavity.

In an embodiment of the invention, the level of energy is limited in accordance with a tooth cavity resistance.

Optionally, the device further comprises a plug for closure of said cavity. Optionally, the plug is movable to define a depth to which said electrode pair extends into said cavity.

Optionally, the controller configured to detect whether the cavity contains conductive fluid, said detecting comprising measuring conductivity between the electrodes.

Optionally, the controller is configured to cut off said current if the absence of said fluid is detected in said cavity.

In an embodiment of the invention, the device is configured with an apex detection unit for detecting the distance of an apex of said cavity from said electrode pair. Optionally, the controller disables pulse generation when the electrode is at the apex.

Optionally, the controller comprises a pulse generator. Optionally, the device comprises a resistance measurement unit for measuring electrical resistance between said electrode pair. Optionally, the controller is operatively connected to said resistance measurement unit, and shuts off said controlled current whenever said electrical resistance is at a level indicating that said electrodes are not currently located in said cavity or the cavity does not contain a liquid There is further provided, in accordance with an embodiment of the invention, a method of treatment of a dental cavity comprising:

inserting a pair of electrodes into said cavity; and generating a controlled energy pulse between said electrodes, in an amount suitable for sterilizing and/or disinfecting said cavity.

In an embodiment of the invention the method includes filling said cavity with a conductive fluid prior to said generating a controlled energy pulse. Optionally, the method includes providing a pulse to dry tissues within said cavity for removal.

In an embodiment of the invention, the method includes measuring a location of an apex of said cavity and setting a mechanical limiter to provide insertion of said electrodes a controlled distance into said cavity responsive to said apex location measurement.

In an embodiment of the invention, the energy is according to a local volume of said cavity.

In an embodiment of the invention, the method includes locating the electrode pair at a first depth in said cavity and providing an energy pulse thereat and then relocating said electrodes to a second depth and an providing an energy pulse thereat.

Optionally, conductive fluid comprises a salt solution. Optionally, the salt solution comprises a salt concentration lying between 0.9% and saturation. Optionally the salt concentration comprises any one of the group comprising a 2% solution, a 3% solution, a 4% solution, a 5% solution, a 6% solution, a 7% solution, an 8% solution, a 9% solution, a 10% solution, an 11% solution, a 12% solution, a 13% solution, a 14% solution, a 15% solution, a 16% solution, a 17% solution, an 18% solution, a 19% solution, and a 20% solution.

Optionally, the conductive fluid comprises one or more of ethylenediaminetetraacetic acid (EDTA hydrogen peroxide, EDTA, chlorhexidine or iodoform (IKI—potassium iodide).

In an embodiment of the invention, the energy pulse causes a breakdown in the cavity that is limited to the cavity.

There is further provided, in accordance with an embodiment of the invention, a method of treatment of a cavity comprising:

inserting a pair of electrodes into said cavity; and generating controlled energy between said electrodes, and therewith disinfecting and/or sterilizing said cavity.

Unless otherwise defined, all technical and scientific terms used herein have the same meaning as commonly understood by one of ordinary skill in the art to which this invention belongs. The materials, methods, and examples provided herein are illustrative only and not intended to be limiting.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
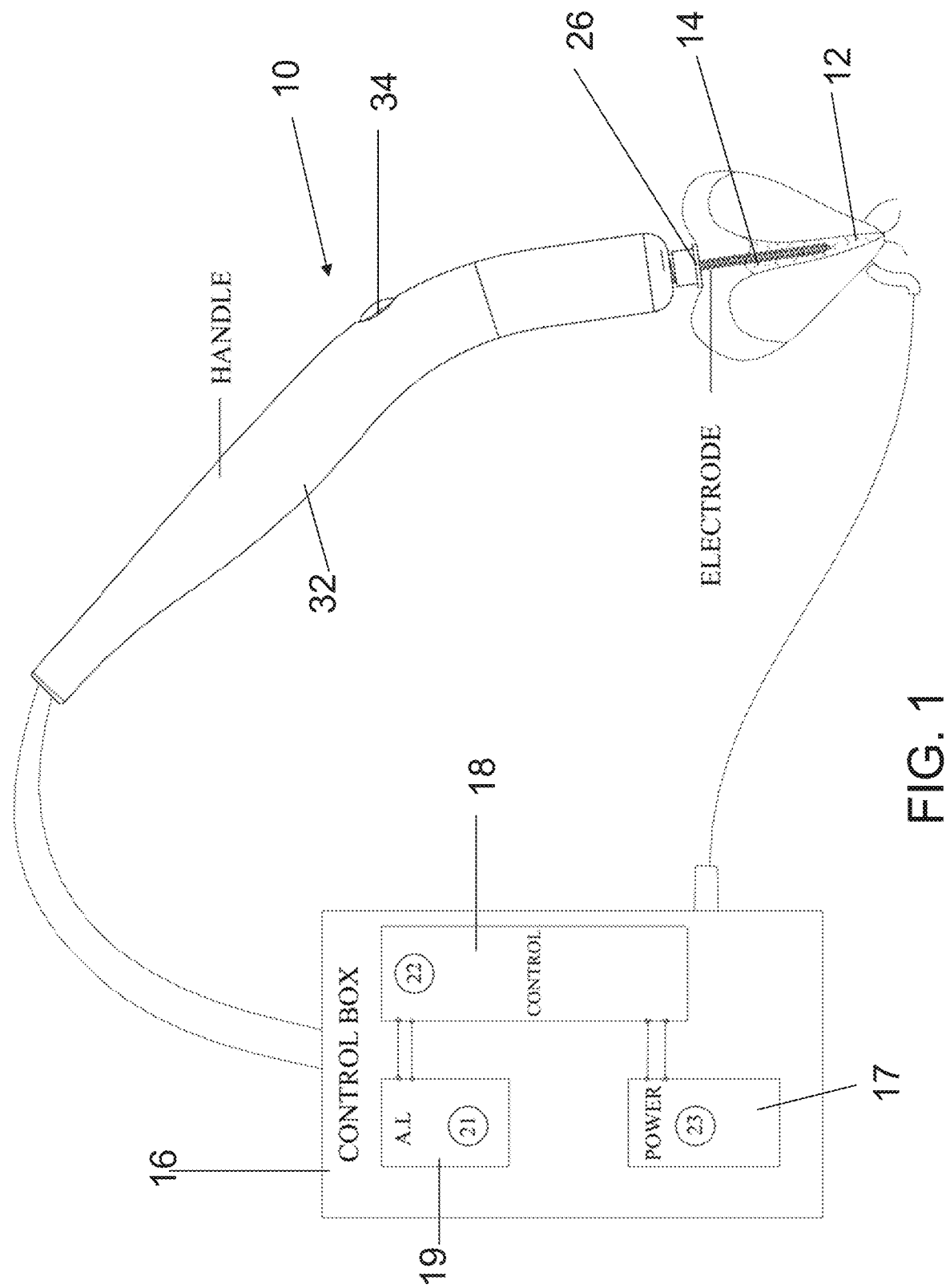
FIG. 1 is a simplified diagram illustrating a first device according to an embodiment of the present invention where electrodes are inserted into a root canal.

The present embodiments comprise an apparatus and a method for root canal sterilization using electrical energy, where an electrode pair is inserted into the root canal. A discharge is induced between the electrodes of the electrode pair. The current is confined to the root canal, and electrical energy is therefore kept out of surrounding tissues. The result is that several Joules of energy can be released within the root canal to kill the bacteria, without detrimental effect on the human body The effect can be enhanced by filling the root canal with either a conductive fluid, such as salt water or an irrigation fluid such as 17% ethylenediaminetetraacetic acid (EDTA), to take two examples. Other fluids with high conductivity and/or sterilizing or disinfecting ability may also be considered. Mixtures of conducting materials and sterilizing or disinfection agents may also be used. In an embodiment of the invention a conductive fluid is placed in the root canal and the electrode pair is dipped or otherwise contacted with a sterilizing or disinfecting fluid. The electrode pair is then inserted into the conducting liquid in the root canal and the current is made to flow between the electrodes. Other sterilizing or disinfecting solutions can be used. Applicants believe that hydrogen peroxide, chlorhexidine, iodoform (IKI—potassium iodide are suitable.

In an embodiment the electrical energy diffuses into the root canal volume and kills the bacteria. The bacteria are killed by one or more of an electromagnetic wave, a wave of heat provided via the liquid and a pressure wave. Although any one of the above may be useful, two or more are preferred for clinical effectiveness and all three together provide the ideal sterilization, thus providing the sterilization.

It is believed that an important factor in the sterilization process is aggressive oxidation cause by the break-up of the water in the solution in which one component is atomic oxygen. The resulting oxidation is very strong compared to that resulting from mere high temperatures. The breakdown caused by the pulse gives rise to pressure and thermal waves which force the atomic oxygen particles into side tubules and channels in the interior of the root. It is believed that many of these tubules and channels are not open during normal sterilization.

Furthermore the electric current generated between the electrodes can be concentrated mainly between the two electrode tips, so the use of energy can be tightly controlled. Thus given precise placing of the electrodes in the root canal it is possible to provide energy at precise locations in the root canal and to vary the energy in accordance with the locations. Furthermore since there is no need to generate an electrical path through the Apex or the tissues of the gums, the energy level can be tailored for the particular location within the canal according to the canal volume and shape.

The principles and operation of an apparatus and method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting. It should also be understood that for simplicity some features are described only with respect to some embodiments. However, combinations of elements from different embodiments are also included in the scope of the invention.

Reference is now made to FIG. 1 which illustrates a device 10 for sterilization of a dental root cavity 12, according to an embodiment of the invention. The device comprises an electrode pair 14 for extending into the cavity.

A controller—control box 16—comprises a power supply 17, a controller 18 and an apex locator unit 19. The power supply includes capacitors to store energy, a voltage supply, a supply limiter and a timer, and provides precise pulses. The controller 18 optionally includes a microprocessor and is able to carry out functions such as measuring apex location within the root canal, measuring conductivity and calculating the pulses needed for the given conditions, in some embodiments of the invention.

The controller 16 sends a controlled electrical current at high voltage to the cavity via the electrodes. The controlled current is confined within the cavity since both electrodes are located within the cavity. The energy released carries out the disinfection. The energy released can be of the order of magnitude of 1 to 10 or even 40 Joules we aren't yet sure, but it will most likely be between 25-40 J, and may be calculated to heat fluid within the cavity within milliseconds to a temperature exceeding 200 or 500 degrees Celsius or at least a temperature exceeding 100 degrees Celsius, to kill any bacteria present. It can be expected that this almost instant heating causes a shock wave within the cavity.

It is noted that to heat the root canal volume, typically approximately 7 micro liters which has been filled with a water based solution to reach 100 degrees Celsius requires approximately two Joules. To evaporate the same volume an additional 16 Joules is needed.

The pulse is optionally a pulse modulated high voltage alternating current whose duration defines the necessary energy levels. The high voltage and the distance between the electrodes define whether breakdown will occur, preferably leading to breakdown.

Figure 2:
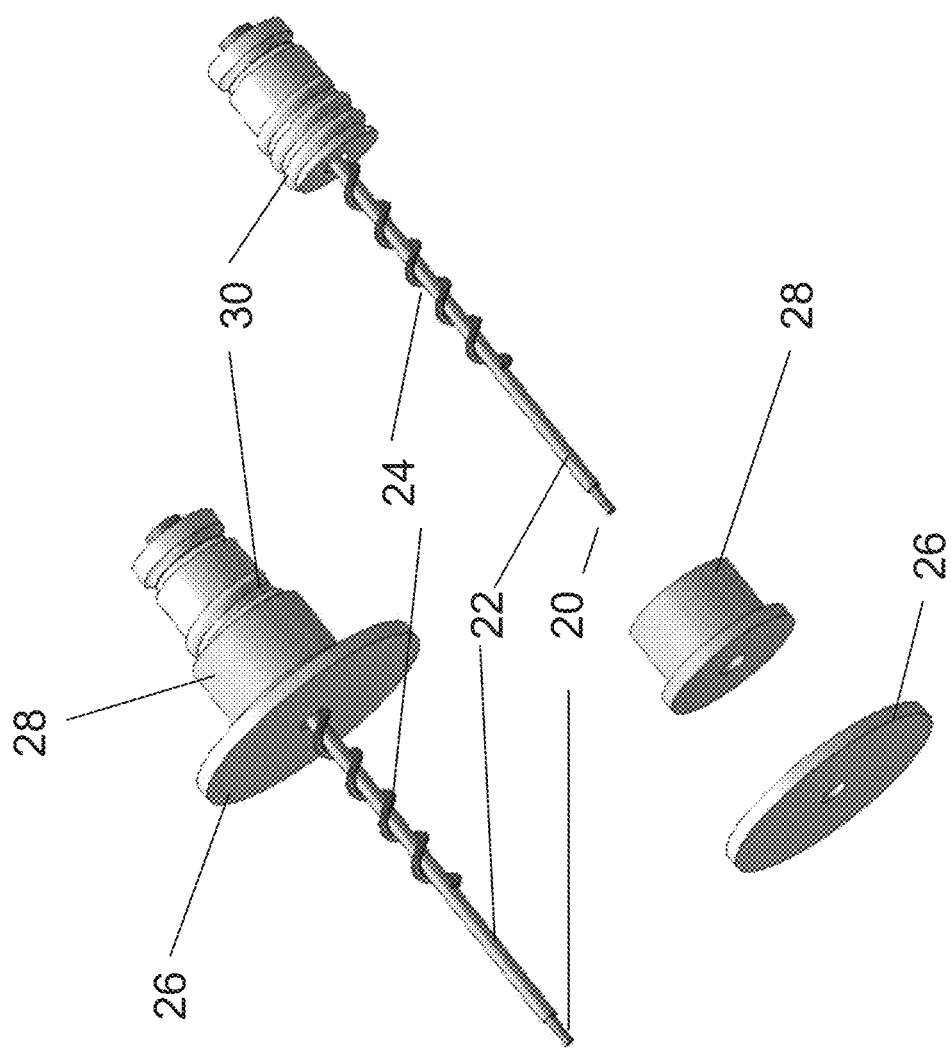
FIG. 2 shows both a detail and an exploded diagram of the electrode assembly of the device of FIG. 1.

Reference is now made to FIG. 2 which is a detail of FIG. 1 showing the electrodes of the electrode pair. A first electrode 20 extends axially within a sleeve 22. Sleeve 22 is an insulator. A tip of the first electrode 20 extends from the sleeve 22. The second electrode 24 of the pair is coiled around the central axis. The electrode construction is made thin enough and flexible enough to be inserted into a root canal. In particular the end of the assembly comes to a point to allow for penetration into the depths of the canal. The head of the axial electrode, meaning the proximal end, has a larger diameter than the distal end, and the outer electrode is wound around the axial electrode. The two electrodes are isolated from each other.

In some embodiments of the invention, the first electrode is controllably extendable along the axial direction, so that the tip can be extended or retracted as desired. The result is to vary the length of a gap between the first electrode and the second electrode and thus control the passage of electrical energy within the canal. The mechanism defines at least two specific lengths of the electrode gap, providing two locations or more in the root canal for releasing energy. Pulses of energy often lead to sparks and the location of the spark is generally in the region between the two ends of the electrodes so that adjusting the height of the first electrode is a relatively accurate way of pinpointing the location of the spark and thus providing precise pinpointing of the energy, from which point the energy spreads around the canal to carry out sterilization.

The controller may alter the current or the voltage or the time or length of the pulses and thus adjust the level of energy released within the cavity. Such an energy level adjustment may be carried out in conjunction with adjustment of the location of the electrode so that greater energy is provided at the outermost end of the root canal and lesser energy at the narrower apex.

It is further noted that the conical shape of the apex tends to decrease resistance and increase the energy at the narrow parts of the canal, thus naturally providing the energy level adjustment even without artificially intervening.

Furthermore the number of pulses in a pulse train is limited so as to reduce the possibility of unintentional energy release after the device has been removed from the root canal.

The construction of the electrode assembly may include a plug 26 which serves to close the cavity, and helps to keep any liquids inside. The plug thus prevents release of fluids heated by the spark. In addition, if any kind of toxic fluid is used then it prevents the release of the toxic fluid into the mouth In an embodiment, the plug is movable to define a depth to which the electrode pair extends into said cavity. As shown the plug is located over rotatable element 28 which can be screwed along thread 30 to provide a finely defined length of the electrode assembly. The length can be set to define the distance to the apex of the root canal so as to prevent the electrodes from being extended into the apex.

In an embodiment the cavity is filled with fluid before insertion of the electrodes, so that the effect of the current is to heat the fluid. The electrodes can be used to measure the resistance in the cavity prior to supply of the current so as to ascertain that the fluid is present. The controller may be set to cut off the current if absence of fluid is detected. In one embodiment there is no separate measurement activity. The first of a train of spark-causing pulses is generated and if the conductivity is too low then it is inferred that the fluid is not present and the remainder of the train is stopped.

The device may be used together with any kind of fluid injector that injects the conductive fluid into the cavity.

The conductive fluid may be a salt solution, say between 2 and 20% saline solution. Alternatively, other fluids, such as EDTA or the other sterilizing or disinfecting materials mentioned herein may be used. Alternatively, mixtures of antibacterial and conducting materials or conducting antibacterial solutions are used. In some embodiments, the cavity is filled with a conducting liquid and the electrodes, carrying antibacterial material are inserted into the liquid. The root canal cavity is very small, of the order of about 7 micro liters in volume, so that very little fluid is in fact present. A small amount of energy can thus heat the fluid very quickly.

As shown in FIG. 2, the central electrode extends beyond both the sleeve and the tip of the outer electrode. A gap between the electrodes of about 7-10 mm is initially defined, however the central electrode can be retracted from this initial position to define different length gaps during the course of the treatment. As mentioned above, the spark generally begins in the region between the two electrodes and thus retraction of the central electrode moves this region and allows for sparks at different locations in the root canal. Since the initial maximum extent is set not to reach the apex, all further treatment is safely away from the apex as well. The spark location can be safely moved within the canal under complete control. Furthermore the amount of energy can be varied according to the present depth. In the deepest parts of the canal the diameter is much smaller and thus less energy is needed than say at the surface.

The amount of power may be arrived at by online measurement of the current and voltage during the pulse train. The constricted space of the canal can only accommodate a limited amount of energy, and increasing the amount of energy beyond this value achieves nothing. However, since increased energy causes heating of the tooth, higher energy inputs may not be desirable. The pulse energy level may thus be limited to the lowest value giving such an upper resistance value for any reason.

Controlling according to the upper resistance value provides for greater energy for greater width and less energy for lesser width.

Overall, a preferred diameter for the central electrode is 0.15 mm. The spiral shape of the second electrode may serve to increase the structural stability of the electrode assembly as a whole.

The device may include an apex locator detection unit which detects the apex of the root canal. Such an apex detection unit is discussed in applicant's copending US Patent Application Publication No. 2008/0187880 A1, the disclosure of which is incorporated by reference. However, any apex detector, as known in the art, may be used in some embodiments of the invention. Alternatively, no apex measurement is made by system 10. Plug 26 serves as a mechanical limiter to limit an extension of said electrode pair into the detected apex.

The controller 16 may comprise a pulse generator and the current may be controlled by varying a size of the pulses generated.

As mentioned, measurement of the resistance measurement between the electrodes is useful for a number of purposes. Thus the controller may include a resistance measurement unit which measures electrical resistance around the extent of the electrode pair. The controller may shut off the controlled current to the electrodes whenever the electrical resistance is at a level indicating that the electrodes are not currently located in the cavity or are located in an apex of said cavity, or when the fluid does not appear to be present.

In an embodiment, the controller supports a pre-disinfection stage of cavity clearing, in which pre-treatment pulses from the electrodes clear dead or dying tissue from the root canal or the walls. Such a pre-disinfection stage may be carried out without artificial insertion of fluid, more specifically prior to insertion of the fluid into the root canal. The natural moisture in the canal may be sufficient. As shown in FIG. 1 (and in greater detail in FIG. 6), the plug 26 is placed over the tooth being treated. Handle 32 is held by the operator to keep the electrode assembly steady within the root canal and button 34 is pressed both to start a train of pulses and to operate the retraction mechanism of the central electrode, so that the pulses can be spread out over at least two locations over the length of the canal.

Figure 3A:
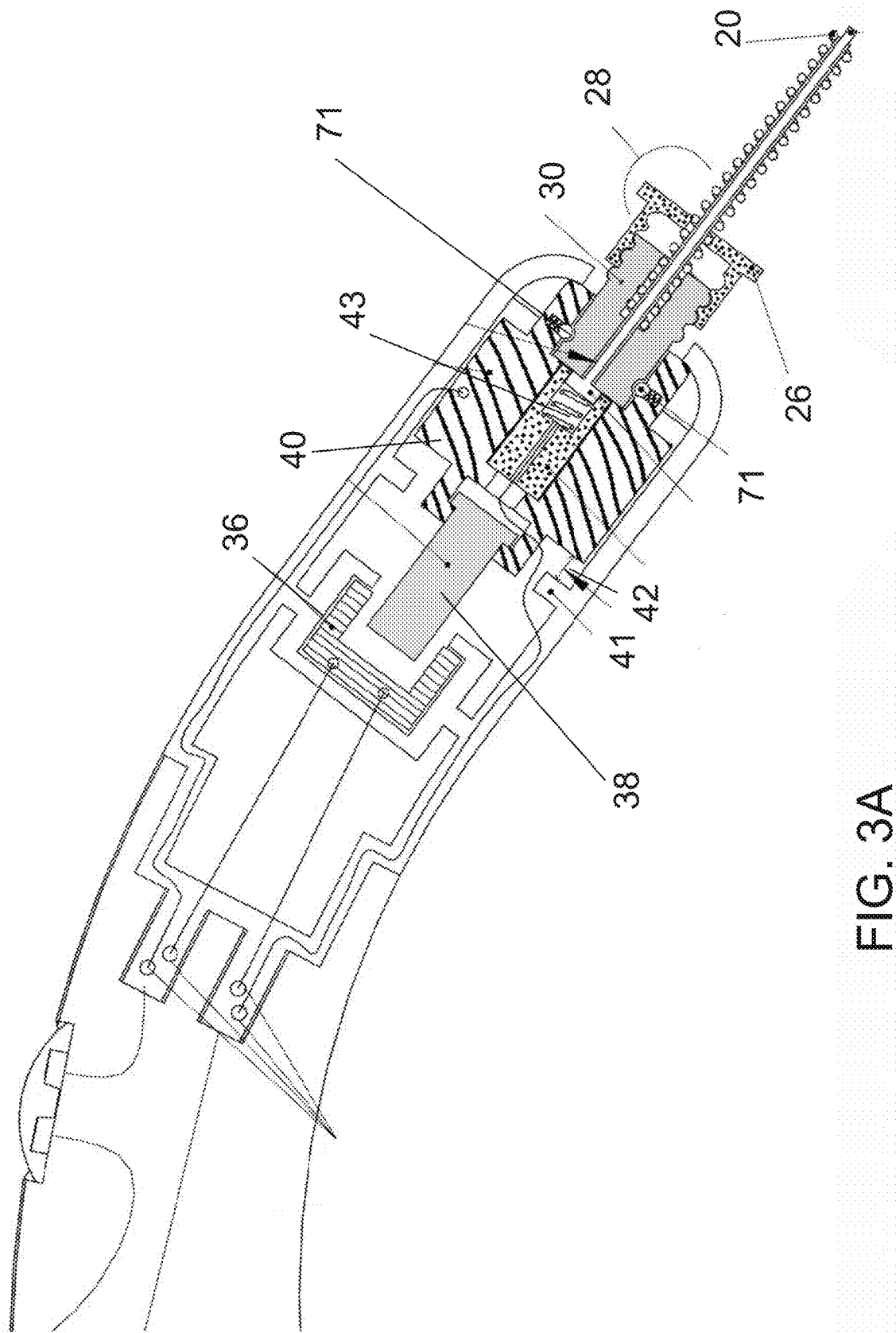
FIG. 3A is a simplified cross section of the handle and electrode moving mechanism of the device of FIG. 1.
Figure 8:
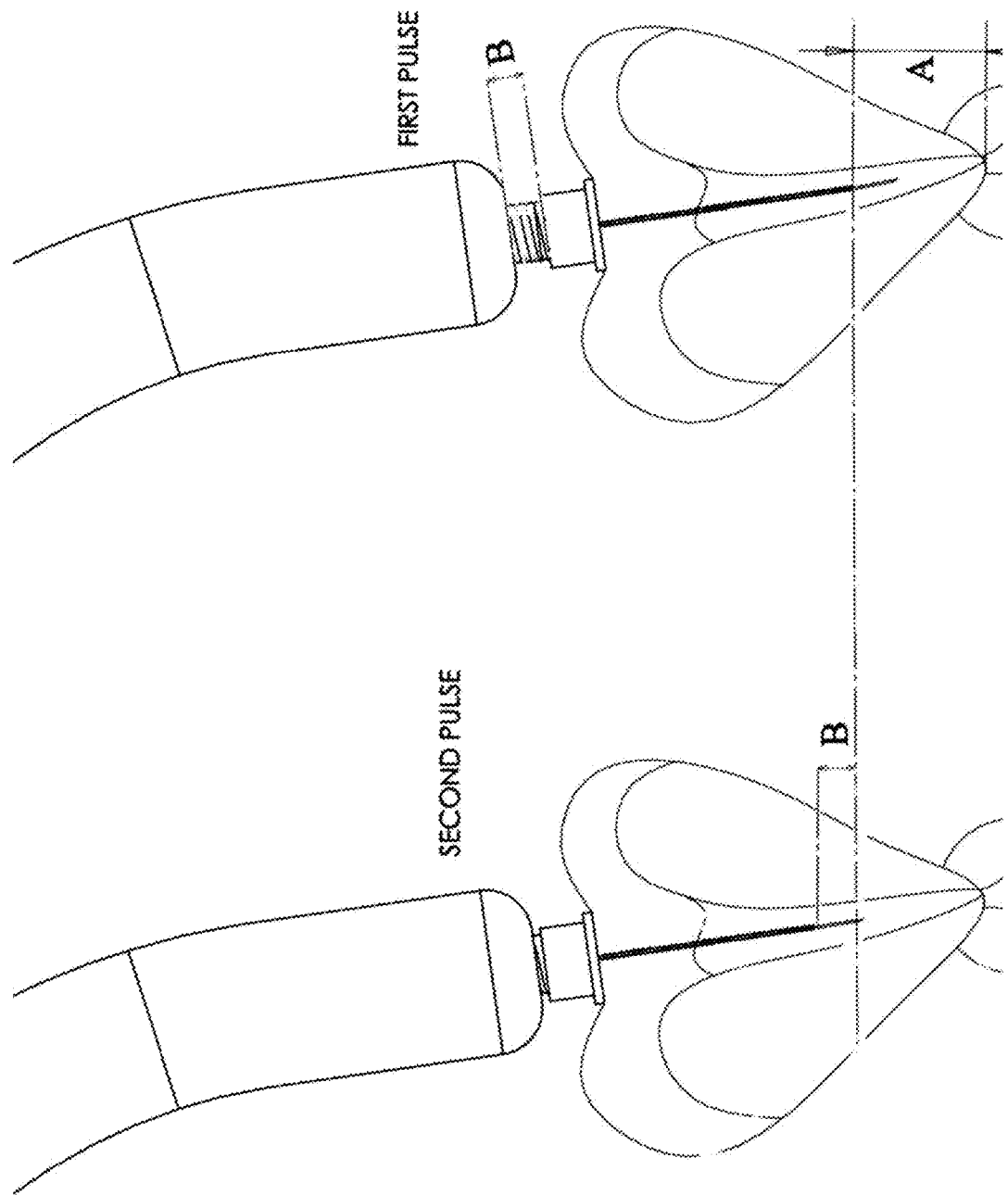
FIG. 8 is a simplified diagram showing the device in the two different positions for the first and second pulse trains respectively according to an embodiment of the present invention.

Reference is now made to FIG. 3A, which is a cross section showing the mechanism of device 10, according to an embodiment of the invention. Parts that are the same as those in figures already described are given corresponding reference numerals and are described further only as necessary for an understanding of the present embodiment. FIG. 3A particularly shows the details of the mechanism for advancing the electrode. Electromagnet 36 is alternatively energized and de-energized to attract or not attract pole 38. Pole 38 takes with it block 40 which is pulled upwards until it reaches step 41, where it is stopped. The arrangement provides for two electrode positions, an upper position and a lower position, as illustrated in FIG. 8 below. The length of slot 42 is chosen for optimal location of the spark along the root canal. Spring 43 ensures an electrical connection to the outer electrode irrespective of the position of the electrode. Button 34 allows the user to operate the controller which will operate the control of the electromagnet and thus the position of the electrode.

Figure 3B:
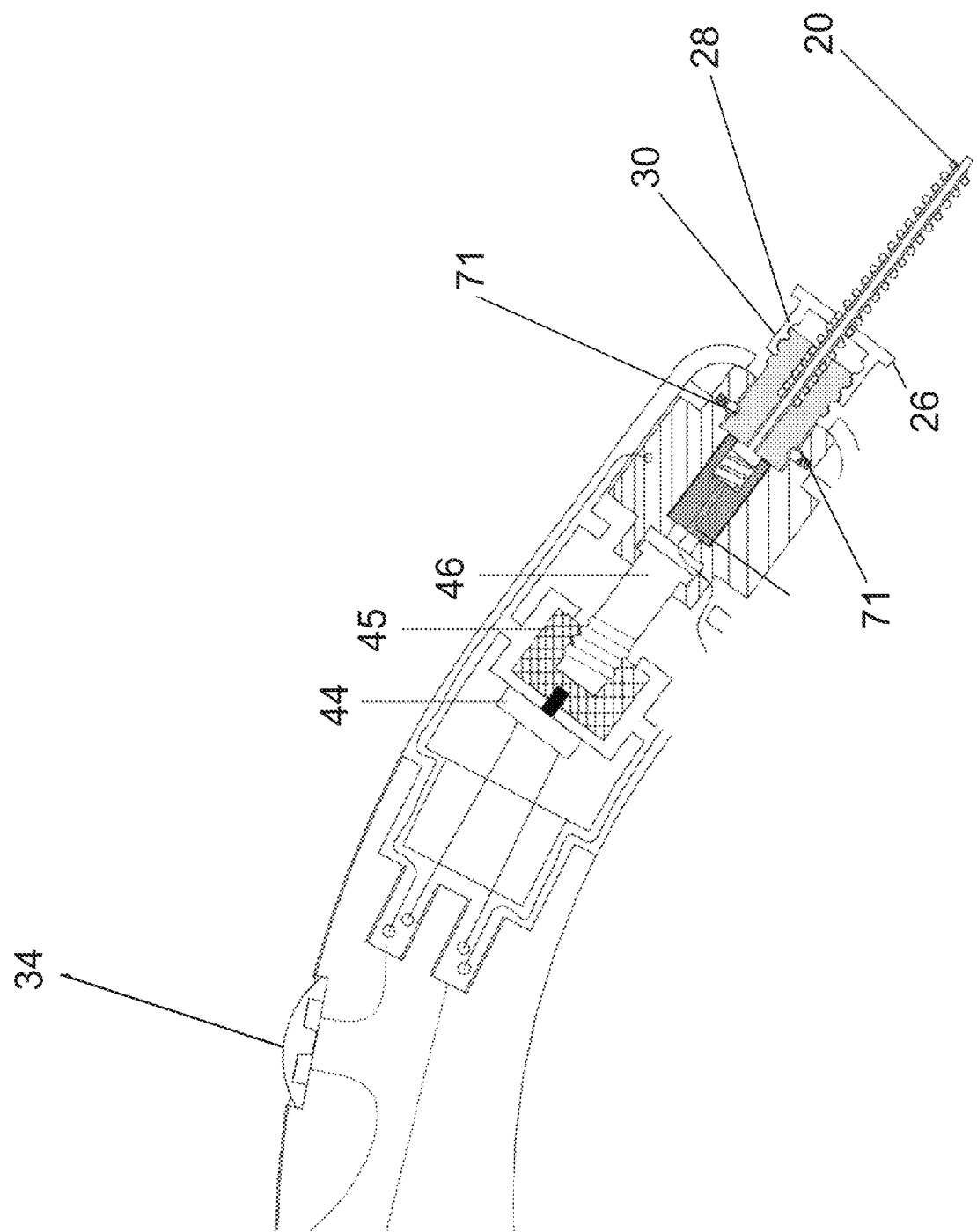
FIG. 3B is an alternative version of the electrode moving assembly of FIG. 3A allowing for multiple electrode positions.

Reference is now made to FIG. 3B, which is a simplified cross-section illustrating a variation of the mechanism of FIG. 3A in which a stepper motor allows a larger number of electrode positions to be attained. Parts that are the same as those in figures already described are given corresponding reference numerals and are described further only as necessary for an understanding of the present embodiment. Stepper motor 44 receives commands from the controller and rotates accordingly. Block 45 rotates and via the mutual thread arrangement advances or retracts pole 46 accordingly in a controlled manner.

Figure 4:
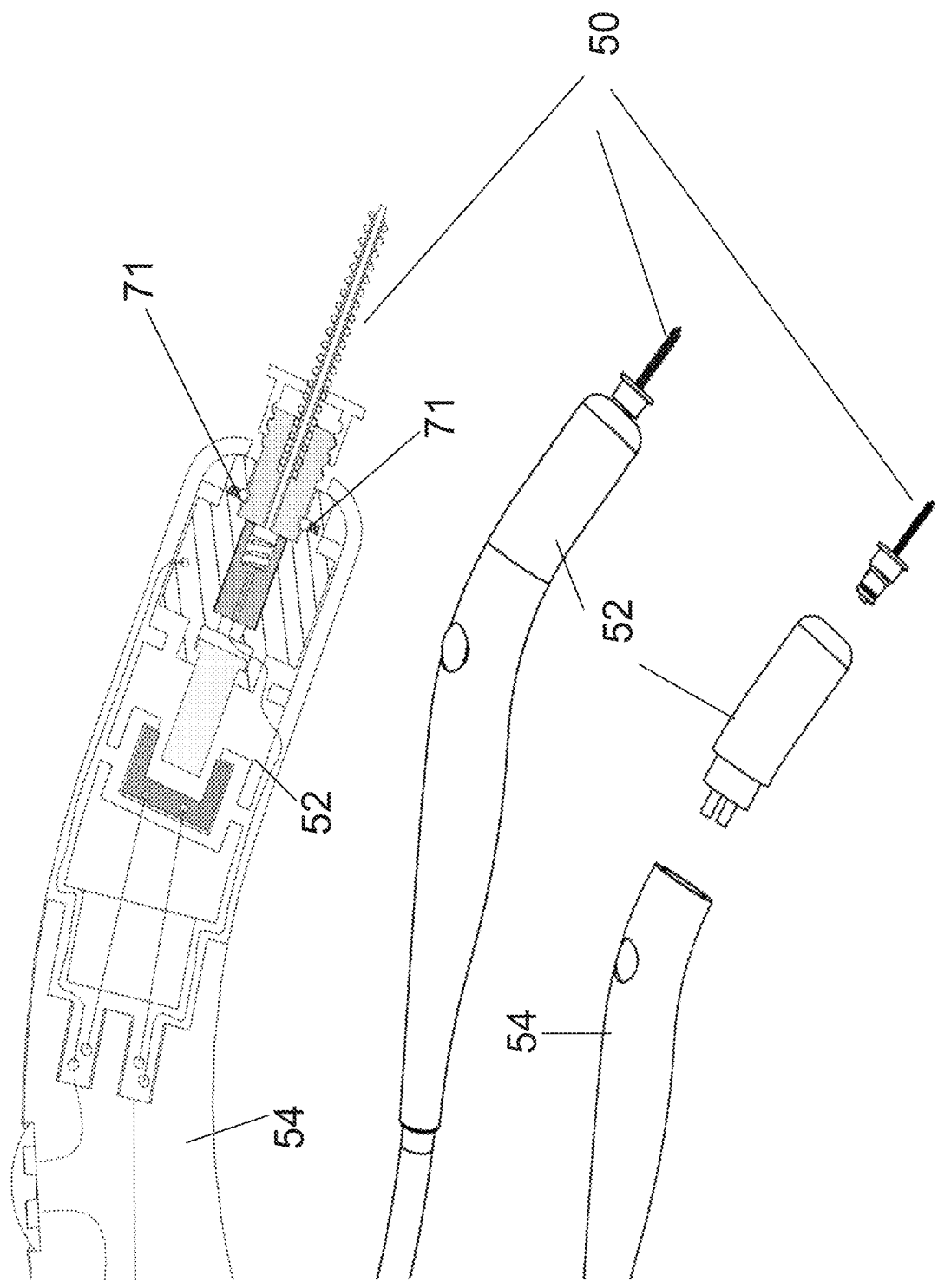
FIG. 4 is another simplified diagram showing the cross section compared to the complete assembly and against the various assemblies separated from each other.
Figure 5:
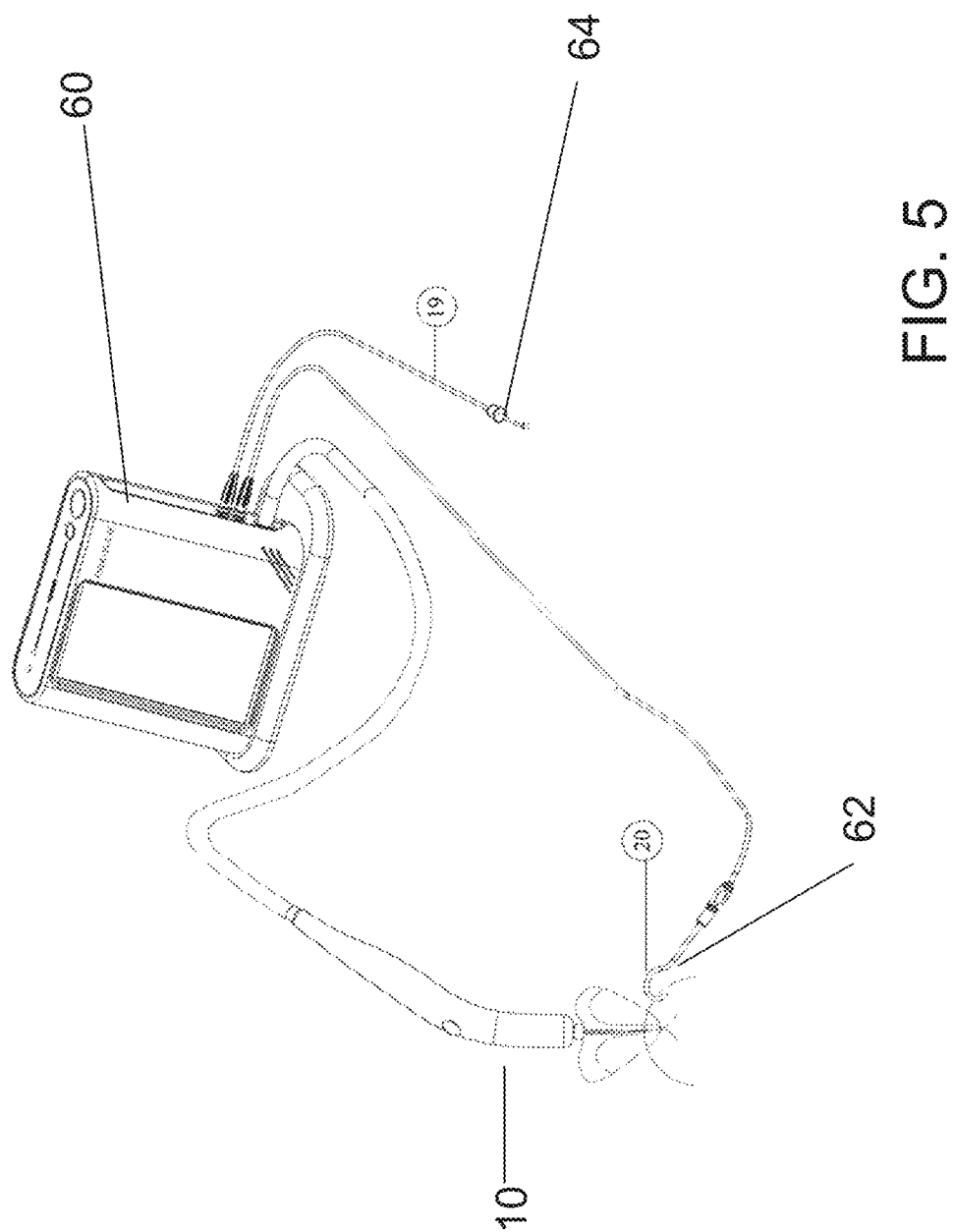
FIG. 5 is a simplified diagram showing the device of FIG. 1 with attachments for apex location, according to another embodiment of the present invention.

Reference is now made to FIG. 4, which shows that the device may be constructed in three parts, the insertion head 50, which includes the electrode assembly and the cap, the electrode control unit 52 which includes the cap mechanism and the plunger mechanism, and the handle itself 54, which is angled for ease of use. The electrode assembly may be removable for sterilization in an autoclave FIG. 5 illustrates an embodiment of a working device. The sterilization device 10 is one of three attachments to a main controller 60 and is inserted into the root canal where electrical sparks are used to sterilize the root canal. Hook 62 is looped on the lip and the combination of hook 62 and attachment 64 are used for locating the apex, in conjunction with the apex location unit.

Figure 6:
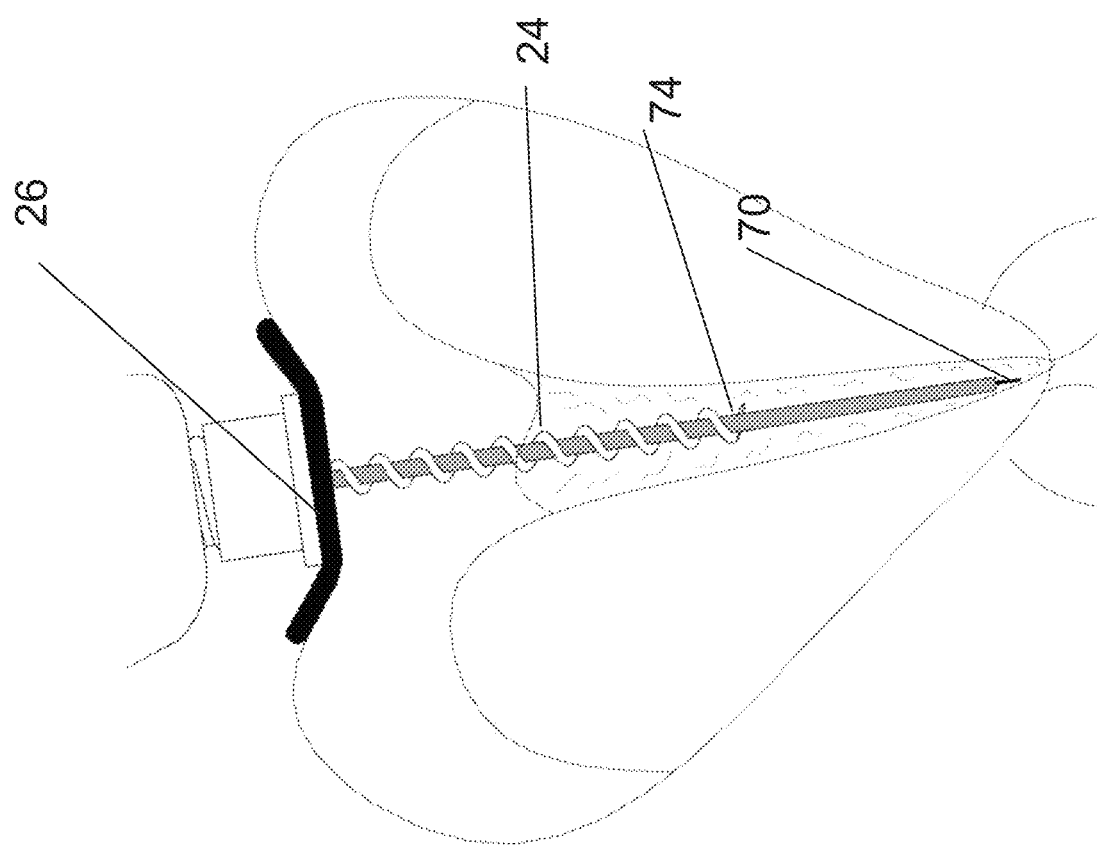
FIG. 6 is a simplified diagram showing in greater detail the electrode assembly of FIG. 1 in the root canal.

FIG. 6 is an enlarged diagram showing the electrode assembly inserted into the root canal. Plug 26 both seals liquids within the tooth cavity and acts as a limiter to prevent the electrodes from reaching the root canal apex. The axial electrode 20 has an exposed tip portion 70. The coiled second electrode 24 has a tip 74. The distance between the tip 74 and the beginning of the exposed portion 70 defines a spark gap, and it is this distance which is varied by moving the axial electrode so that the precise location of the spark can be varied during the therapy as described above in respect of FIGS. 3A and 3B. The sleeve is fixed with the electrode assembly 50 which is fixed in place by holders 71.

A prototype using the above energy levels managed to sterilize a root canal having a high concentration of bacteria, of the order of $10^{-6}$, which is equivalent to a highly infected root canal.

Figure 7:
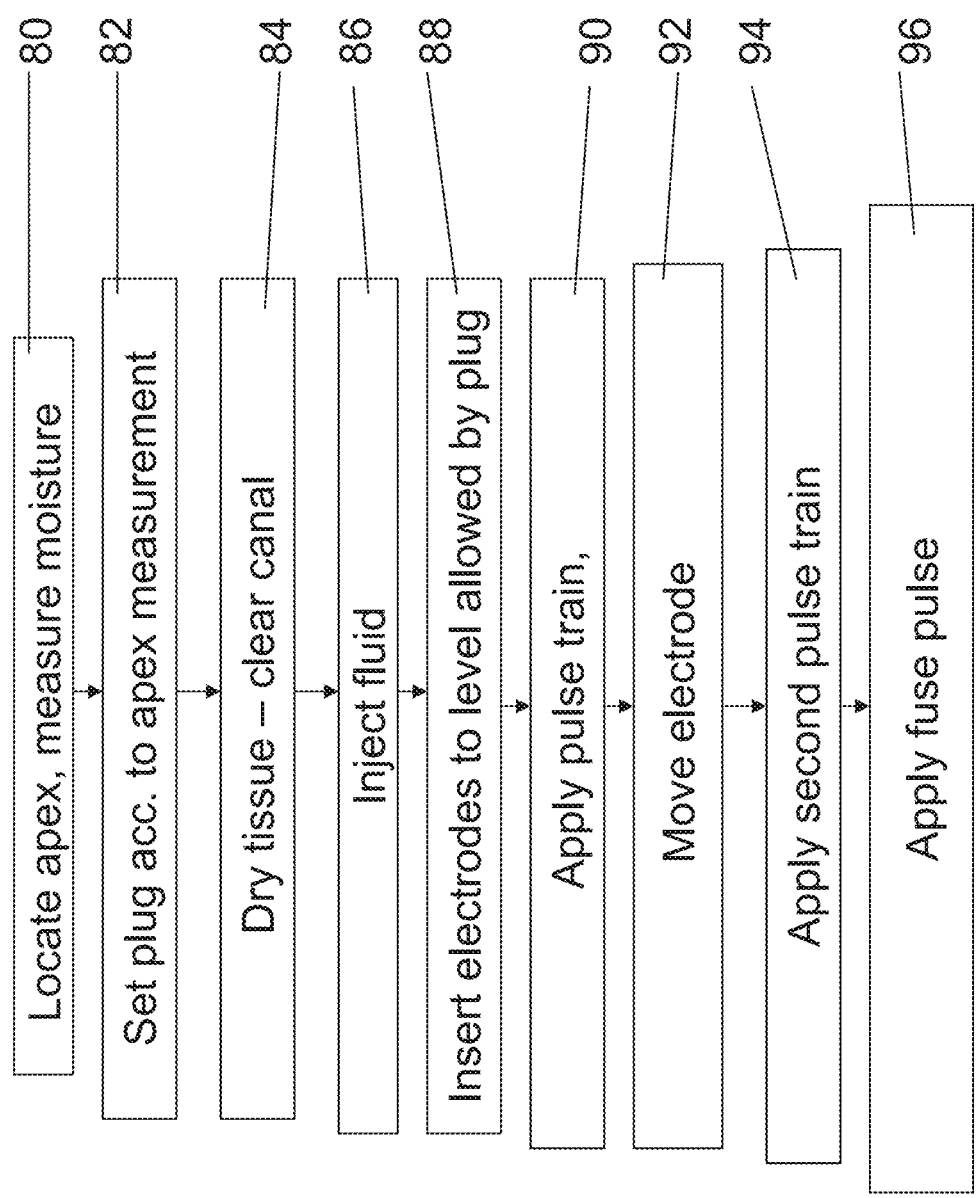
FIG. 7 is a simplified flow chart showing the operation of a device according to an embodiment of the present invention.

A process for use of the device is now described with respect to FIG. 7. The process begins with stage 80 by locating the apex using the apex locator attachment 19 and hook 62. Alternatively, the location of the apex (referenced to the top of the tooth) is determined using a separate apex locator. At the same time as the apex is located the moisture level of the root is measured and fed directly into the operating program. In stage 82, plug 26 is then rotated to define the depth of the apex so as to act as a guard against the electrodes being inserted into the apex. Preferably the plug is set to give a predetermined distance of clearance from the apex, one or two or more millimeters of clearance. For example, initial clearance of 3-4 millimeters appears to be suitable.

An intermediate stage 84 of providing an initial pulse based on partial penetration of the electrode device into the canal can optionally be carried out in order to dry the tissues of the canal which will need to be removed by the files prior to sterilization. Drying the tissues eases their subsequent removal. The size of pulse needed to dry the tissues may be obtained from the detected moisture level of the canal as detected previously.

The optional conductive and/or cleaning and/or disinfecting fluid may be injected into the root canal in stage 86.

The electrode assembly is now attached to the handle and inserted into the channel until further progress is impeded by the plug, in stage 88. In some embodiments of the invention, the electrode assembly is dipped in a disinfectant or antibacterial material before being inserted into the liquid in the root canal.

The dentist then presses on the button 34, which operates the control program in the controller. The control program issues one or more pulses of defined power depending on the location of the electrode within the canal and the size of the canal—the apical constriction. When the volume of the canal is lower, the power in the pulses will be lower. The voltage level of the pulses is controlled to affect the overall power as is the timing of the pulses. The pulse train may stop when the program is completed. As a safety feature, in an embodiment of the invention, a single push-button operates the system, with a first push of the button causing a set of capacitors to charge and a second push causing the capacitors to discharge into the cavity. As an additional safety feature, a waiting period between pulse trains is preferably required, for example a wait of 45 seconds between pulse trains. A typical number of pulses for the train would not exceed four although it is envisioned that a larger number such as 6 could be used. Between pulse trains, the root canal is preferably rinsed and refilled with liquid.

Once the control program has completed the train of pulses for the deeper part of the root canal—stage 90, the plunger is operated to move the electrodes to the higher part of the canal, further from the apex—stage 92. In stage 94 a further pulse train is produced, and here greater power is used as the size of the canal is larger. If needed additional liquid is added and/or the electrode assembly is dipped in disinfectant or antibacterial material before stage 94. As mentioned above the amount of power is arrived at by online measurement of the current and voltage. The pulse energy level may thus be limited to to a value giving a desired energy.

Finally, in stage 96, a large pulse is optionally supplied to disable the electrodes and stop further activity. The large pulse is a safety feature intended to ensure that electrical energy is not inadvertently released outside the root canal, say in contact with the jaw or the molars.

A further safety feature involves the ability to detect inadvertent entry of the electrodes into the apex for whatever reason, say human error in setting the plug. The apex locator mechanism continually operates via a small current through the electrode 20 sent to hook 62, of the order of 10 mA. A danger area is defined and whenever the electrodes are indicated to be in that danger area the pulse train is automatically shut down.

An additional safety feature ensures that the actual energy of the pulse does not exceed the calculated energy.

Reference is now made to FIG. 8 which illustrates the device of the present embodiments in two pulse positions in the root canal The device is initially extended as far as plug 26 will allow, which means that the electrode reaches deep into the root canal, and almost up to the apex. The first pulse or pulse train is issued at this first deep position—position A. Then the electrode is retracted, for example using the mechanism of FIG. 3A above, and the second pulse or pulse train is emitted at position B. Optionally, a single pulse train or multiple pulse trains at a single position (for example, 3-4 mm from the apex) is sufficient to provide sterilization.

A device according to the present embodiments may have a number of advantages over the existing systems that use electrodes.

First of all there is no heating of tissues outside the root canal. Rather all the energy is concentrated in the region that requires sterilization. Furthermore there is no nerve stimulation outside the region of treatment. Thirdly there is no need to subject the patient to the psychological trauma of having the other electrode clearly in view and being felt. Furthermore the safety features that are needed are fewer than for the existing devices.

As a further safety feature, the energy of the pulse is limited by the upper resistance threshold of the cavity.

Figure 9:
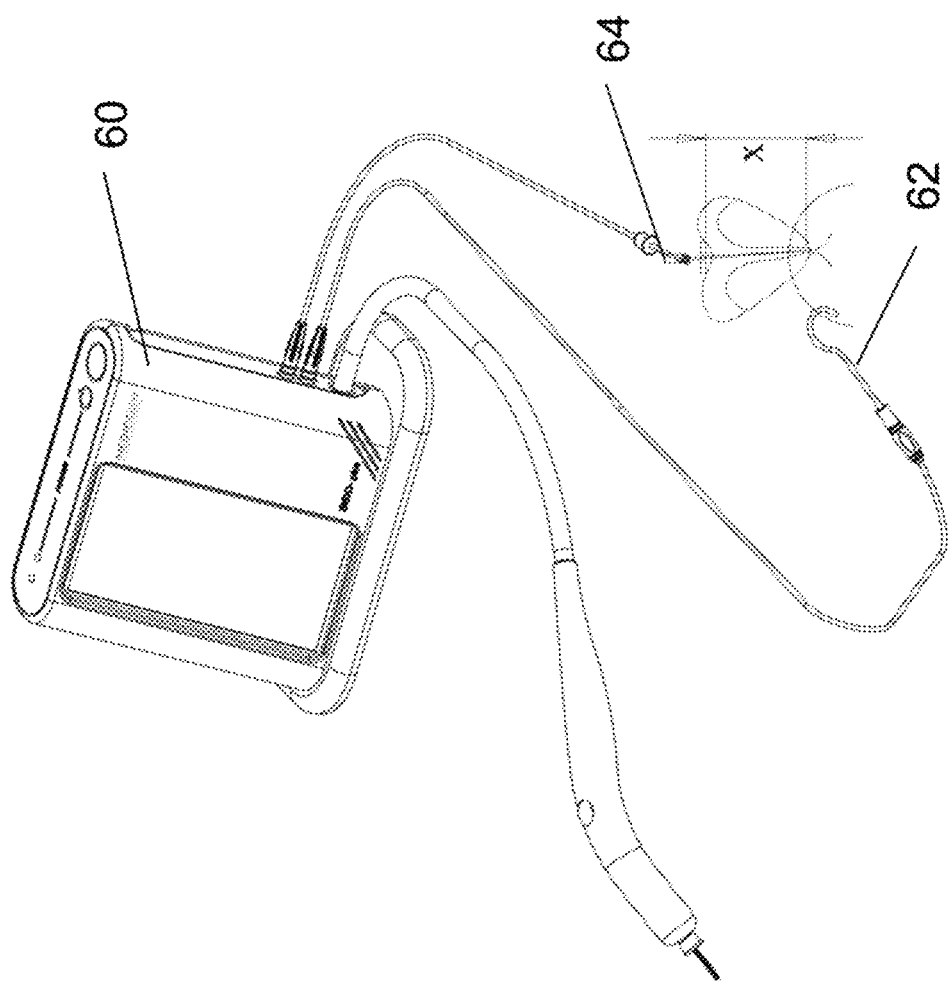
FIG. 9 is a simplified schematic diagram which shows use of attachments for apex location in order to set the position of the electrode in the root canal.

FIG. 9 is a simplified schematic diagram which shows use of attachments for apex location in order to set the plug. Parts that are the same as in earlier figures are given the same reference numerals and are only explained again in accordance with the need to understand the present figure. The process of locating the apex is controlled within controller 60. Hook 62 is placed on the gum to define a ground and then a train of high frequency pulses are released into the canal from apex location attachment 64. The reflection of the pulses is measured. A second train of pulses is then emitted at a different frequency and the reflection is measured. The two reflections are subjected to signal processing and then applied to a look up table which supplies a number, that number being the length of the canal. The user then sets the plug to give an electrode length according to (in fact slightly less than) that number in millimeters. The preferred process is more fully described in applicant's copending International Patent Application No. PCT/IL2007/000755, the contents of which are hereby incorporated by reference.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treatment of a root canal having a longitudinally variable diameter and longitudinal curvature within a tooth comprising:
    filling said root canal with a disinfectant fluid;
    inserting an insulator and a pair of electrodes into said root canal and said disinfectant fluid,
    said pair of electrodes including an outer electrode external to said insulator and exposed to said fluid along a length of said insulator and a second electrode said second electrode including an insulated portion located within said insulator and an exposed portion extending distally from a distal end of said insulator into an apical portion of said root canal and exposed to the disinfectant fluid;
    generating an electrical energy pulse creating a spark in the disinfectant fluid along a length of the canal between said outer electrode and said exposed portion of said second electrode.

2. The method of claim 1 wherein the method includes winding said outer electrode around said insulator.

3. The method of claim 1, wherein the energy pulse causes a breakdown in the root canal in a gap of between 7 to 10 mm between said exposed portion of said second electrode and said outer electrode and is limited to the root canal.

4. The method of claim 1 wherein the energy pulse causes a breakdown in the root canal generally along a length of the canal, that is limited to the root canal.

5. The method of claim 1, further comprising
    measuring a location of an apex of said root canal;
    setting a mechanical limiter to provide insertion of said exposed portion of said second electrode a controlled distance into said root canal, responsive to said apex location measurement; and
    moving said pair of electrodes in relation to said limiter.

6. The method of claim 5, further comprising: closing the canal and keeping liquids inside the canal by means of a plug and wherein said limiter includes said plug.

7. The method of claim 1, further comprising
    controlling said energy pulse according to a local volume of said root canal between said outer electrode and said exposed portion of said second electrode.

8. The method of claim 7, comprising
    locating said outer electrode at a first depth in said root canal and
    providing the energy pulse thereat and then relocating said outer electrode to a second depth while said disinfectant fluid remains in the canal and providing a further energy pulse at said second depth.

9. The method of claim 1, wherein said disinfectant fluid includes a salt solution.

10. The method of claim 9, wherein said salt solution comprises a salt concentration lying between 0.9% and saturation.

11. The method of claim 1 wherein said disinfectant fluid comprises one or more of hydrogen peroxide, EDTA, chlorhexidine or iodoform (IKI—potassium iodide).

12. The method of claim 1, further comprising providing an electrical pulse to dry tissue from the canal before said filling, said generating and said disinfecting.

13. The method of claim 1, further comprising retracting said second electrode to adjust a length of a gap between said outer electrode and said exposed portion of said second electrode.

14. The method of claim 1, wherein said outer electrode is fixed to said insulator.

15. The method of claim 1, further comprising: increasing a structural stability of the insulator and second electrode with said outer electrode.

16. A method of treatment of a root canal having a longitudinally variable diameter and longitudinal curvature within a tooth comprising:
    inserting a flexible pair of electrodes with an insulator into a fluid in the canal, said pair of electrodes including an outer electrode external to said insulator and exposed to said fluid along a length of said insulator and a second electrode, said second electrode including an insulated portion located within said insulator and an exposed portion of the second electrode from a distal end of said insulator into an apical portion of said root canal and exposed to the fluid;
    generating an electrical energy pulse between said outer electrode and said exposed portion of said second electrode;
    limiting said energy pulse to an amount of energy that can be accommodated by a constricted space of the canal;
    causing a breakdown of fluid within the root canal as a result of said energy pulse;
    producing a pressure wave within said root canal as a result of said breakdown;
    forcing disinfecting material in said fluid by means of said pressure wave into a channel not open to said any of said outer electrode and said second electrode; and
    disinfecting said channel utilizing said breakdown wherein said disinfecting material is limited to the root canal and channel.

17. The method of claim 16, further comprising providing an electrical pulse to dry tissues within said root canal for removal of said tissues before said generating and said disinfecting.

18. The method of claim 16, further comprising:
    varying a length of a gap between said exposed portion of said second electrode and said outer electrode according to the constricted space of the canal while said outer electrode and said exposed portion of said second electrode are inside said canal.

19. The method of claim 16, wherein said outer electrode is fixed to said insulator.

20. The method of claim 16, further comprising: increasing a structural stability of the insulator and second electrode with said outer electrode.

* * * * *